(12) United States Patent
Schöb

(10) Patent No.: US 6,864,084 B2
(45) Date of Patent: *Mar. 8, 2005

(54) BIOREACTOR AND METHOD FOR FLUIDLY SUSPENDING A PRODUCT

(75) Inventor: Reto Schöb, Volketswi (CH)

(73) Assignee: Levitronix LLC, Waltham, MA (US)

( * ) Notice: Subject to any disclaimer, the term of this patent is extended or adjusted under 35 U.S.C. 154(b) by 117 days.

This patent is subject to a terminal disclaimer.

(21) Appl. No.: 10/004,194

(22) Filed: Oct. 31, 2001

(65) Prior Publication Data

US 2002/0037580 A1 Mar. 28, 2002

Related U.S. Application Data

(63) Continuation-in-part of application No. 09/655,203, filed on Sep. 5, 2000, now Pat. No. 6,632,658.

(30) Foreign Application Priority Data

Aug. 18, 2000 (EP) .............................. 00810734

(51) Int. Cl.$^7$ .............................. C12M 3/02; C12N 5/00
(52) U.S. Cl. ............................... 435/293.1; 435/286.5; 435/295.1; 435/302.1; 435/1.2; 435/403
(58) Field of Search .............................. 435/295.1, 383, 435/302.1; 422/140–142; 366/274

(56) References Cited

U.S. PATENT DOCUMENTS

| | | | |
|---|---|---|---|
| 2,083,348 A | * 6/1937 | Scholler et al. | ........... 435/295.2 |
| 4,978,616 A | 12/1990 | Dean, Jr. et al. | |
| 5,320,963 A | * 6/1994 | Knaack et al. | ............ 435/295.1 |
| 5,445,073 A | * 8/1995 | Gilwood | ........................ 99/427 |
| 5,501,971 A | * 3/1996 | Freedman et al. | ........... 435/393 |
| 5,538,162 A | * 7/1996 | Reh et al. | ..................... 222/63 |
| 6,100,618 A | * 8/2000 | Schoeb et al. | ............. 310/90.5 |

FOREIGN PATENT DOCUMENTS

| | | |
|---|---|---|
| EP | 0472223 A1 | 2/1996 |
| WO | WO 86/00636 A1 | 1/1986 |

OTHER PUBLICATIONS

Ver, Leah May B., "Design Criteria of a Fluidized Bed Oyster Nursery", *Aquacultural Engineering*, vol. 14, No. 3, pp. 229–249, (1995).

Maruyama, Toshiro, et al., "Liquid fluidization in conical vessels", *The Chemical Engineering Journal*, 46, 15–21 (1991).

\* cited by examiner

*Primary Examiner*—William H. Beisner
(74) *Attorney, Agent, or Firm*—Townsend and Townsend and Crew LLP

(57) ABSTRACT

A method for floating at least one substance for growing a tissue part in a bioreactor. The method includes providing at least one substance consisting of one of a tissue part, a scaffold having cells deposited thereon, and a scaffold including a tissue part thereon. The method further includes further acting upon the substance with fluid, wherein the fluid holds the substance in free floatation. The fluid flows in a direction counter to gravity when a density of the substance is greater than a density of the fluid, and in a direction counter to buoyancy when a density of the substance is less than a density of the fluid. The bioreactor for floating at least one substance for growing a tissue part includes a container including a first flow chamber and at least one substance consisting of one of a tissue part, a scaffold having cells deposited thereon, and a scaffold including a tissue part thereon. The substance is acted upon with fluid. The bioreactor further includes an apparatus for conveying the fluid. The substance is arranged in the first flow chamber in such a manner that the fluid holds the substance in free floatation.

41 Claims, 11 Drawing Sheets

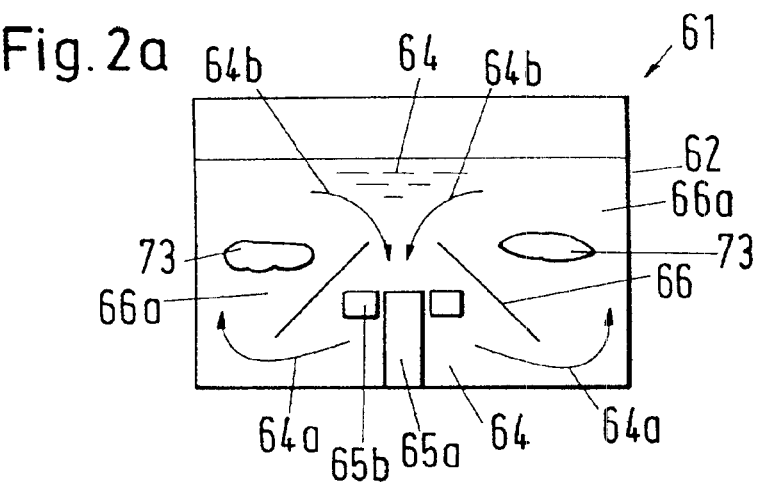
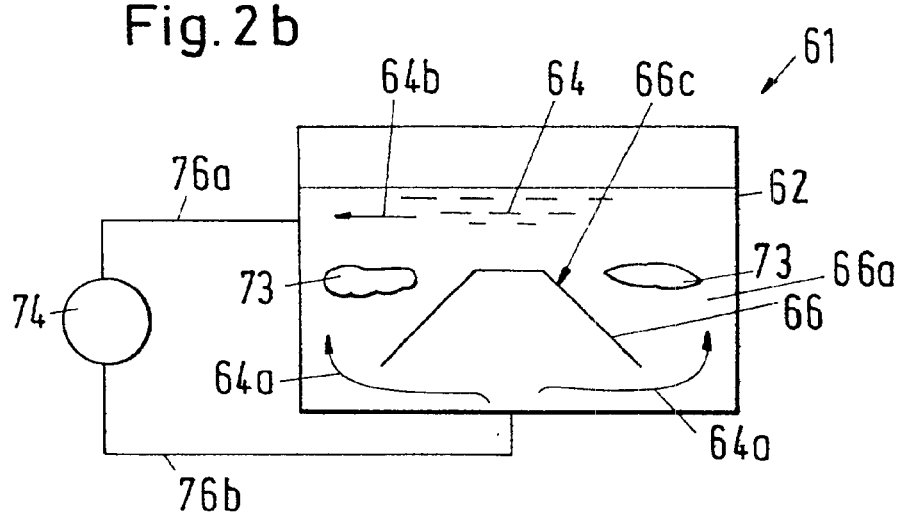
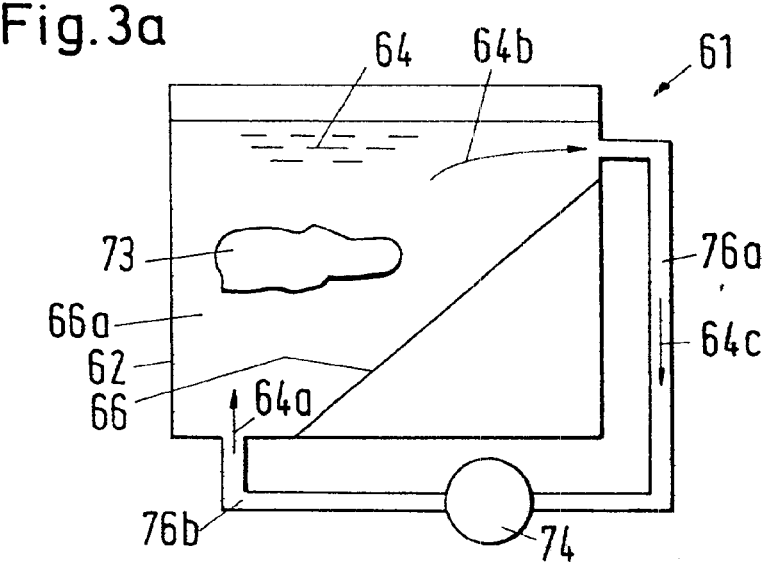

B-B

A-A

D-D

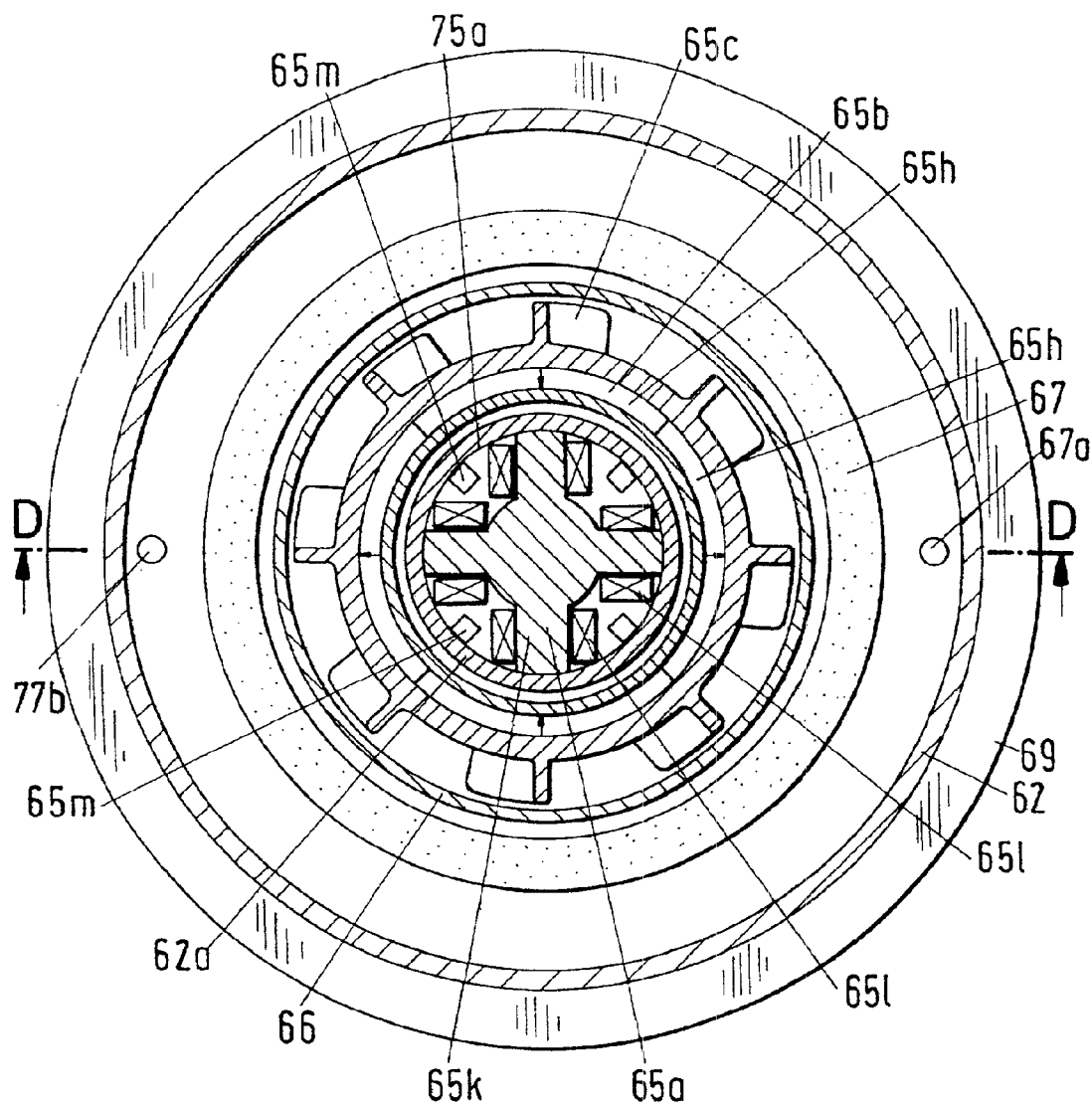

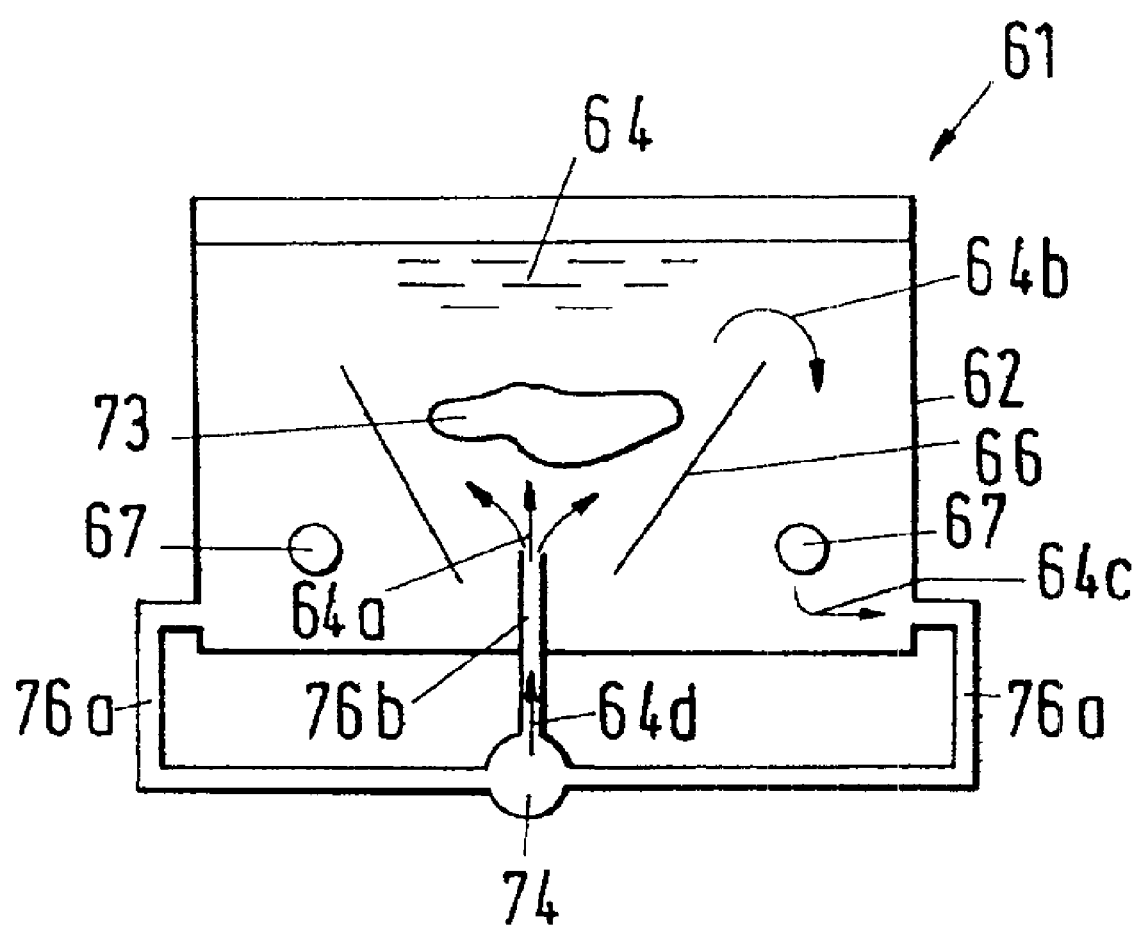

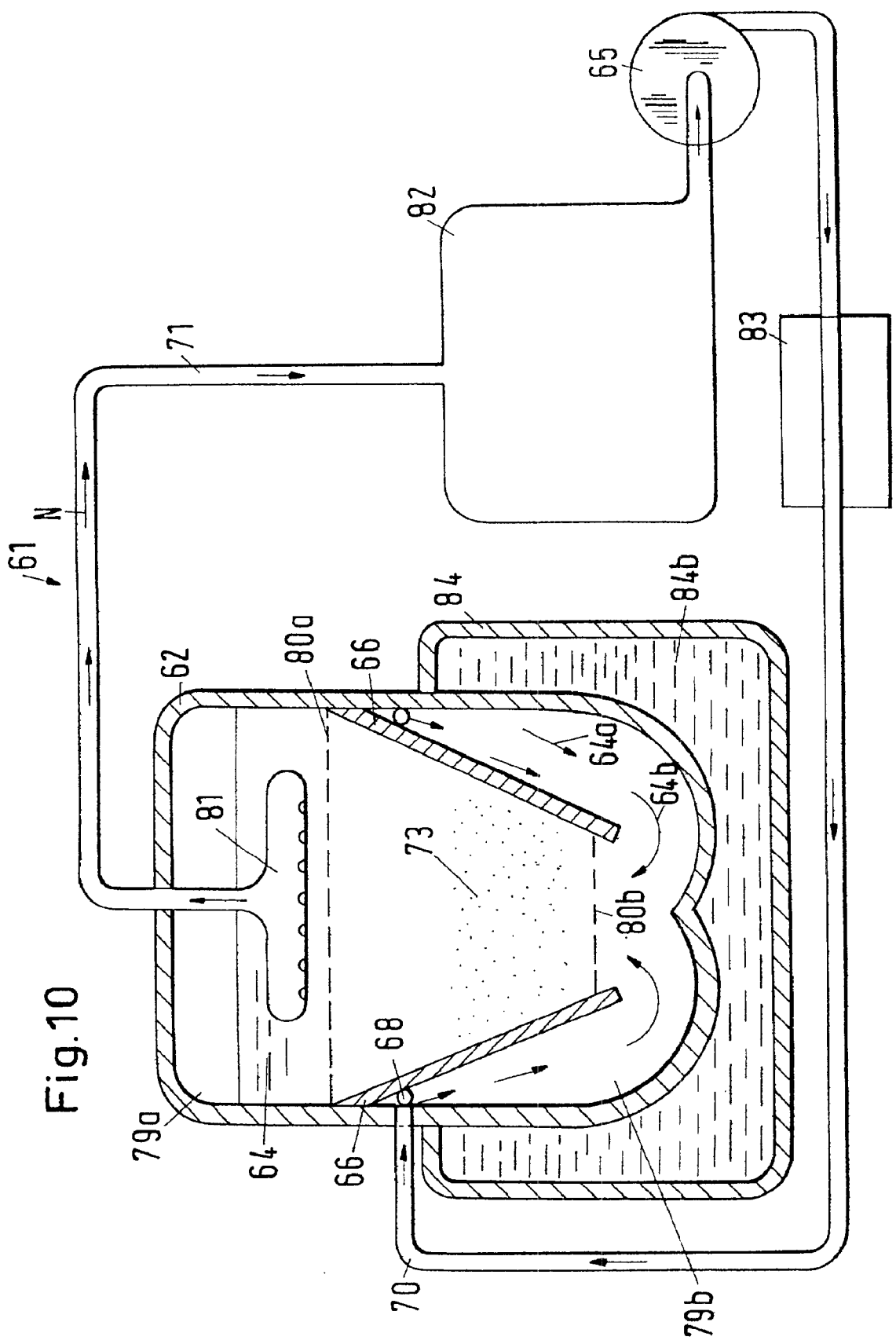

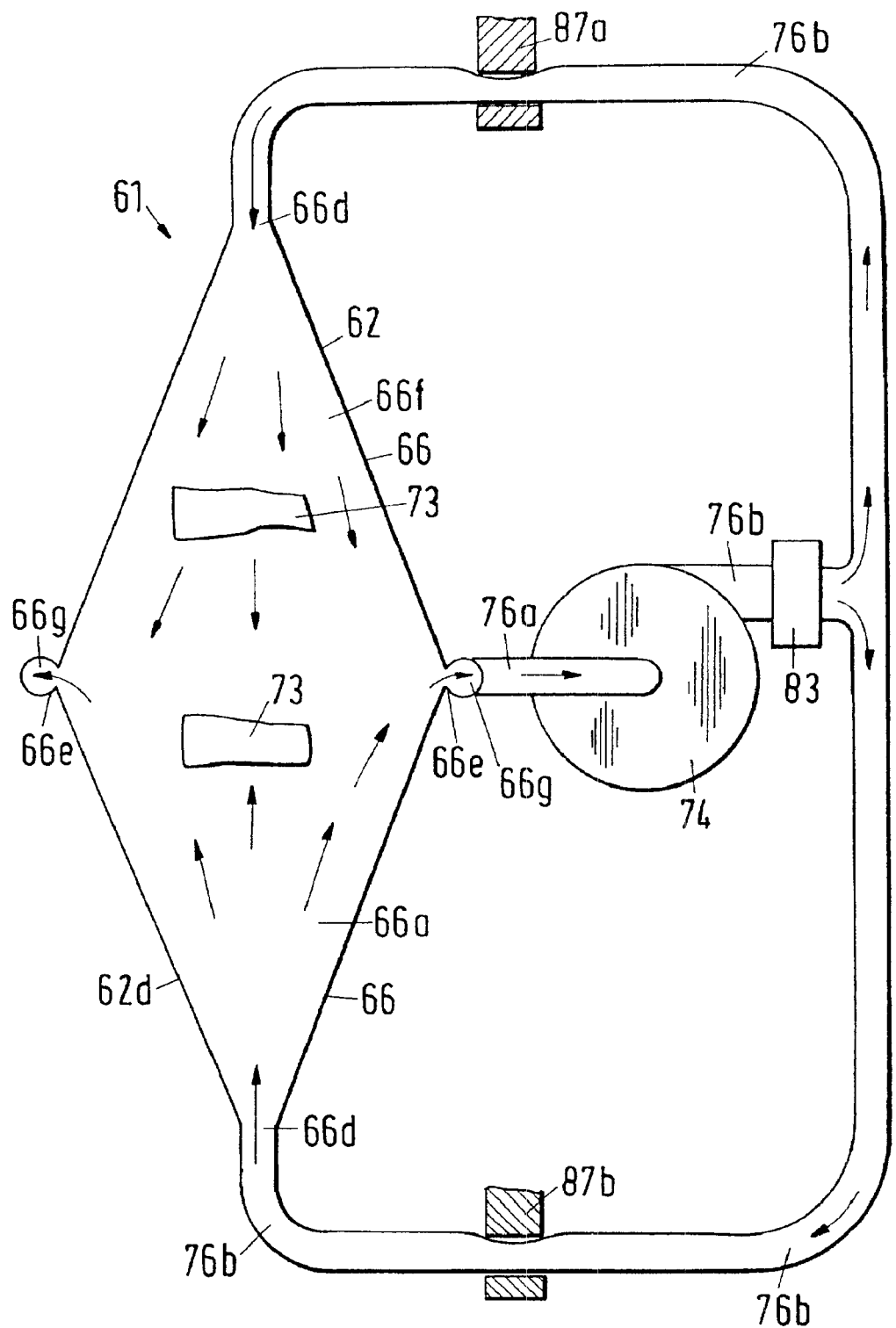

_US 6,864,084 B2_

BIOREACTOR AND METHOD FOR FLUIDLY SUSPENDING A PRODUCT

RELATED APPLICATION

This application is a continuation-in-part application of U.S. patent application Ser. No. 09/655,203, filed Sep. 5, 2000, now U.S. Pat. No. 6,632,658, and titled "BIOREACTOR AND METHOD FOR FLUIDLY SUSPENDING A PRODUCT".

BACKGROUND OF THE INVENTION

The invention relates to a method for holding a substance in suspension and to a bioreactor for holding a substance in suspension.

The artificial production of tissue material, designated in English as "tissue engineering", is increasingly gaining in importance in order to produce biological substitutes for damaged tissue or damaged organs. Artificial tissue material can be produced in that cell cultures in vitro are deposited at or in a tissue carrier, also termed a matrix. The tissue carrier consists for example of a synthetic polymer or of a biological material such as collagen. A tissue carrier of this kind is also designated as a "scaffold". The cells are sown out onto the tissue carrier and begin to multiply if the environmental parameters are physiologically favorable. The tissue carrier can be designed in such a manner that the latter disintegrates with time, so that after a certain time only the tissue part which is formed from the cells is present. The tissue carrier and/or the tissue which is formed on it is designated as "substance" in the following. The conditions which are required for the cell growth are produced in a bioreactor, within which the required oxygen and a nutrient medium are supplied to the substance and within which the substance remains from several days to weeks until the desired size has been reached. The geometrical shape which the artificially produced tissue material assumes during growth is substantially influenced through the measures by means of which the substance is held in the bioreactor.

Thus in the following the term "substance" will be understood to mean both the tissue carrier per se and the tissue carrier with cells deposited on it, or, if the tissue carrier is designed to be decomposable, the artificially produced cell culture or the artificially produced tissue part respectively.

SUMMARY OF THE INVENTION

The object of the present invention is to propose a method for holding a substance in a bioreactor which enables an advantageous growth. It is furthermore an object of the present invention to propose a bioreactor which has advantageous properties with respect to the growth of cell cultures.

The object is satisfied in particular by a method for the holding in suspension of a substance in a bioreactor in that the substance is acted upon with a fluid and the flow of the fluid acts counter to gravity or buoyancy in such a manner that the substance is held in suspension.

The method in accordance with the invention has the advantage that the substance is held without contact in the bioreactor in that the fluid, usually a liquid, has a flow which is developed in such a manner that the substance is held without contact by the flow, which acts counter to gravitation. In this the substance is usually also kept continually in motion so that its position changes continually. The method in accordance with the invention has the advantage that the cells grow uniformly at or in the substance respectively and the growth of the substance is favored. Disadvantageous in the previously known methods for the artificial production of tissue is that it had been possible to produce only flat, substantially two-dimensional structures.

In a particularly advantageously designed method the fluid has an increasingly slower flow speed in the direction opposite to gravitation. This flow behavior is for example produced in that the flowing fluid is led from below into a hollow body having the shape of a truncated cone which widens upwardly. The cross-section of the hollow body, which widens upwardly, causes the flow speed in the hollow body to be reduced with increasing height. The substance is continually held in suspension in the inner space of the hollow body, with the side walls of the hollow body limiting a lateral movement of the substance, so that the substance is always located in the upwardly flowing liquid. With increasing cellular growth the weight of the substance increases, so that the substance moves slightly downwards in the inner space of the hollow body and finds again a new equilibrium position there. The substance thus automatically seeks the respective equilibrium position. It can however prove advantageous to monitor the position of the substance with a sensor and to influence the speed of the upwardly flowing fluid by means of the measured signal. Thus the speed of the fluid can for example be regulated in such a manner that the substance is continually held in suspension in a predetermined position.

In an advantageous method, in addition to the upward flow within the bioreactor a downward flow is also produced, with a gaseous fluid such as air or oxygen being supplied to the downwardly flowing fluid, usually a liquid. The speed of the downwardly flowing fluid is advantageously chosen such that the gaseous fluid which is input is slowed down or no longer rises at all, so that the gaseous fluid remains relatively long in the flowing fluid and can be taken up or absorbed respectively by the latter.

The object in accordance with the invention is further satisfied in particular by a bioreactor comprising a container for a substance which is to be acted upon with a fluid, with the container comprising a first flow chamber to which a flowing fluid can be supplied and with the first flow chamber being designed in such a manner that the fluid which flows upwardly therein has a lower speed with increasing height. In a particularly advantageous design the flow chamber has a cross-section which widens upwardly.

In a further advantageous design a flow guiding means is arranged within the bioreactor and forms a flow chamber which widens upwardly. In addition this flow guiding means preferably forms a further, second flow chamber within the bioreactor, with the second flow chamber diverging downwardly and with a gaseous fluid being introduceable into the second flow chamber.

In a further, advantageous embodiment a drivable pump wheel is arranged within the bioreactor, with the help of which the flow of the fluid within the bioreactor can be produced. The pump wheel is advantageously magnetically coupled to a drive which is arranged outside the housing of the bioreactor. The bioreactor housing and the pump wheel are advantageously conceived as a disposable or once-only product respectively so that the latter can be disposed of after a single use. These parts can be manufactured economically. For example the pump wheel comprises a vaned wheel of plastic into which is cast a permanent magnet. All expensive components such as the drive apparatus are arranged outside the bioreactor. The design of the bioreactor as a disposable product has the advantage that no laborious cleaning process is required and that a contamination of the artificially produced tissue material is largely excluded. The avoidance of contamination is of decisive importance since the substance remains for example 4 to 8 weeks in the bioreactor, until sufficient tissue material has been formed. Since the bioreactor has no immune reaction system, the smallest contaminations such as bacteria, fungi or viruses can already result in the produced artificial tissue dying off or being contaminated. Through the design of the bioreactor as an expendable product, artificial tissue material can be economically and reliably produced.

The invention will be explained in the following with reference to a plurality of exemplary embodiments.

BRIEF DESCRIPTION OF THE DRAWINGS

FIGS. 2a, 2b are longitudinal sections through further exemplary embodiments of bioreactors;

FIGS. 3a-3d are longitudinal sections through further exemplary embodiments of bioreactors;

FIG. 8 is a section through FIG. 7 along the line C—C;

FIG. 9 is a longitudinal section through a further bioreactor;

FIG. 10 is a longitudinal section through a further bioreactor;

FIG. 11 is a longitudinal section through a further bioreactor.

DETAILED DESCRIPTION OF SPECIFIC EXEMPLARY EMBODIMENTS

Figure 1:
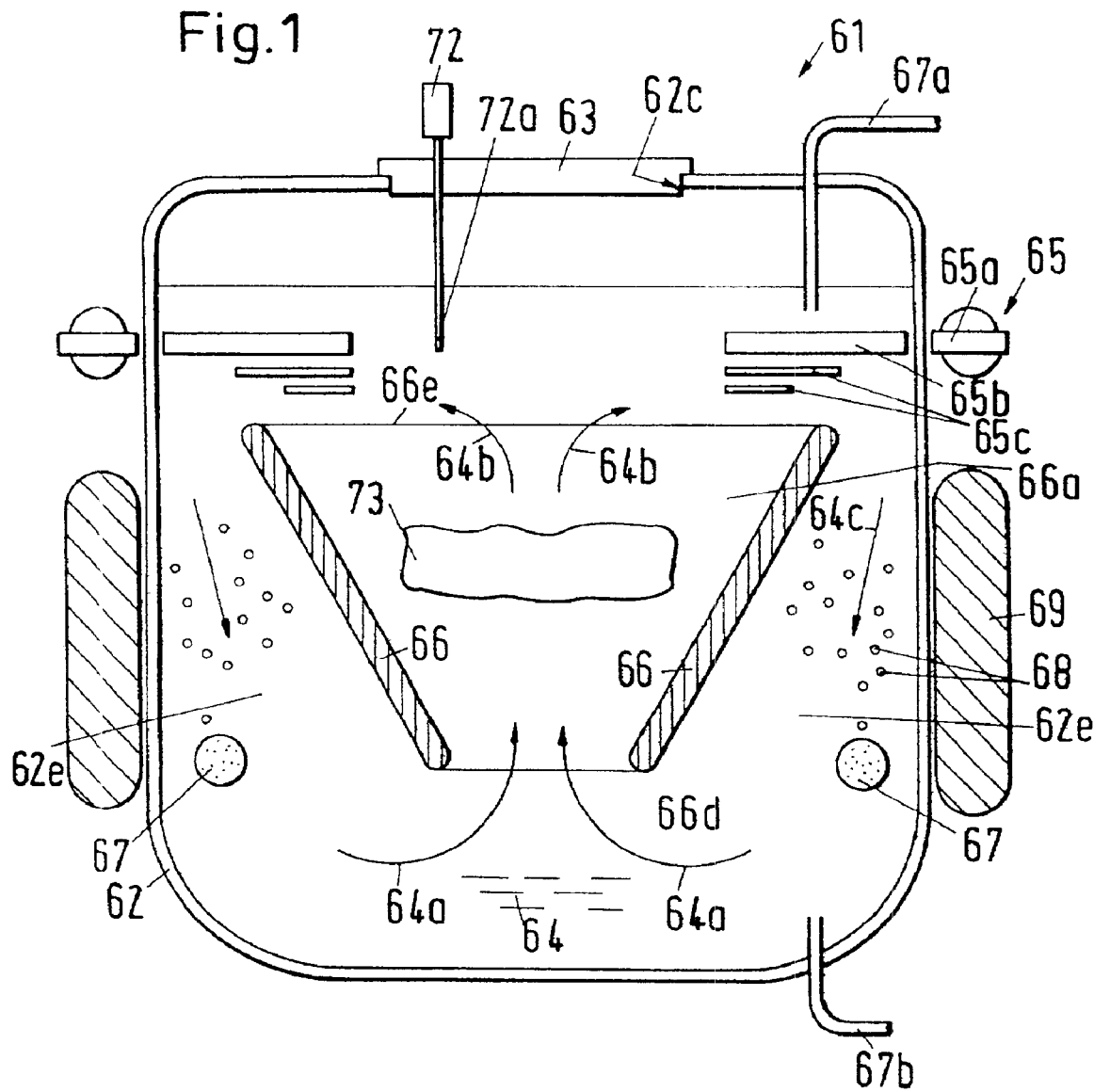
FIG. 1 is a longitudinal section through a first bioreactor.

The bioreactor 61 which is illustrated in FIG. 1 comprises a container 62 which has an opening 62c at the top, which can be closed by a closure 63. Arranged in the inner space of the container 62 is a flow guiding means 66 having the shape of a truncated cone which is formed as a hollow body, the cross-sectional area of which increases upwardly. The inner space of the container 62 is largely filled with a liquid 64, which is set into a circulation flow by the vaned wheel 65c of the motor 65, so that the liquid 64 has the flow direction which is illustrated by the arrows 64a, 64b, 64c. The liquid which flows in the direction of the arrows 64a enters from below with relatively high flow speed via the entry opening 66d into the inner space 66a of the flow guiding means 66, flows upwards in the inner space 66a with decreasing speed, and leaves the inner space 66a at the top again with relatively low flow speed through the outlet opening 66e, as illustrated by the arrows 64b. In the inner space 66a the flow speed decreases as a result of the upwardly widening cross-section. The inner space 66a forms the first flow chamber. If the diameter of the outlet surface 66e is for example twice as great as the diameter of the inlet surface 66d, then the speed at the outlet surface 66e corresponds to one-fourth of the speed at the inlet surface 66d. The buoyancy force which is caused by the flow speed still amounts at the outlet surface 66e to one-sixteenth of that at the inlet surface 66d. The substance 73, which is arranged in the inner space 66a, is held in an equilibrium position through the upwardly flowing liquid, with the suspension level, i.e. the equilibrium position of buoyancy force and gravitation, setting in by itself as a result of the weight and the working surface of the substance.

Arranged above the flow guiding means 66 is a pump 65, which comprises an iron stator 65a which is arranged outside the container 62 and a rotor 65b which is arranged within the container 62. A vaned wheel 65c is firmly connected to the rotor 65b. An apparatus of this kind comprising a stator and a rotor which is held and driven by magnetically acting forces is also designated as a bearingless motor and is known to the skilled person, for example from the specification WO 96/31934.

The vaned wheel 65c produces the circular flow which is illustrated with the arrows 64a, 64b, 64c. Formed between the container 62 and the flow guiding means 66 is an inner space 62e, also designated as second flow chamber, having a cross-sectional area which widens downwardly. This has the result that the liquid which flows downwardly in the flow direction 64c has a flow speed which decreases downwardly.

Arranged at the bottom in the inner space 62e is a ring-shaped distributor 67, through which air or oxygen is led in for the gasification of the liquid 64, which forms air bubbles 68 within the liquid 64 which have the tendency to rise. Through the liquid, which flows downwardly in the direction 64c, the rising of the air bubbles 68 is delayed or prevented, which furthers the gas exchange to the liquid 64.

The container 62 is surrounded on the outside by a ring-shaped heating apparatus 69. The inner space of the container 62 is supplied via an inlet line 67a and an outlet line 67b with a nutrient liquid. A measurement probe 72 with probe head 72a enables for example a monitoring of the pH value or the temperature of the liquid 64.

The bioreactor 61 illustrated in FIG. 1 has the advantage that the substance 73 is easily accessible via a closure 63 having a large diameter.

Figure 1A:
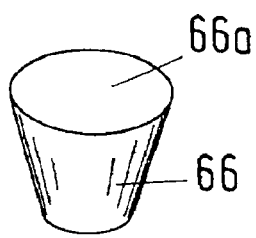
FIG. 1a is a perspective detail view of the flow guiding means.

FIG. 1a shows a perspective illustration of the flow guiding means 66 with inner space 66a.

FIG. 2a shows schematically a longitudinal section through a further exemplary embodiment of a bioreactor 61, which differs with respect to the example which is illustrated in FIG. 1 in that the flow guiding means 66 is arranged in reverse, which means with a downwardly widening cross-section. The pump 65 comprising the iron stator 65a and the rotatable part 65b with vaned wheel 65c causes a flow in the direction 64a, 64b in the liquid 64. The inner space 66a, in which the liquid flows upwards, and in which the substance 73 is held, is located between the flow guiding means 66 and the outer wall of the container 62.

FIG. 2b shows schematically a longitudinal section through a further exemplary embodiment of a bioreactor 61, which differs with respect to the example which is illustrated in FIG. 2a in that the flow guiding means 66 is designed to be seated at the top and that the fluid pump 74 is arranged outside the container 62, with the pump 74 being connected in a fluid conducting manner to the inner space of the container 62 via lines 76a, 76b. The fluid which flows in the direction 64a enters from below into the inner space 66a and flows around the substance 73.

FIG. 3a shows schematically a longitudinal section through a further exemplary embodiment of a bioreactor 61, which likewise has a fluid pump 74 which is arranged outside the container 62 and which is connected to the inner space in a fluid guiding manner via lines 76a, 76b. The flow guiding means 66 is designed to be upwardly widening only on the one inner side of the container 62. The substance 73 is held in suspension through the liquid which circulates in the direction 64a, 64b, 64c in the inner space 66a.

Figure 3C:
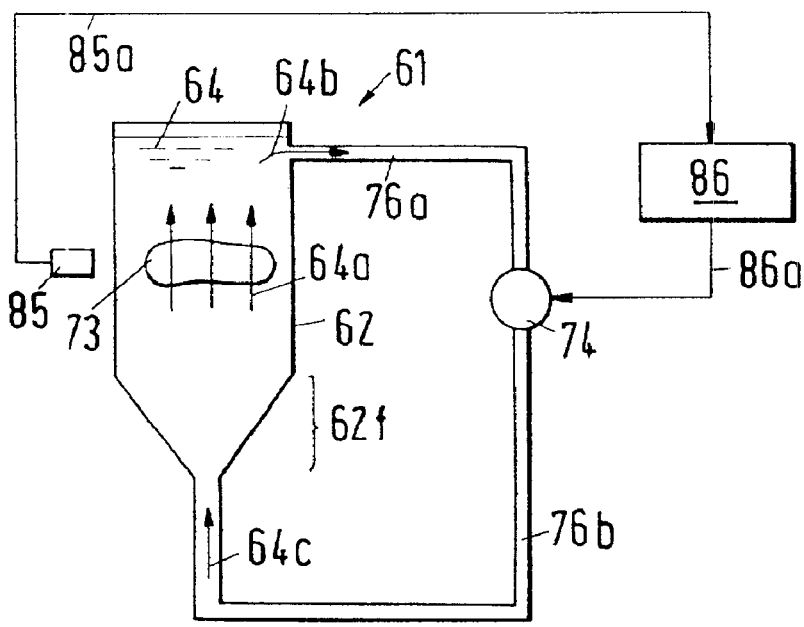
Figure 3B:
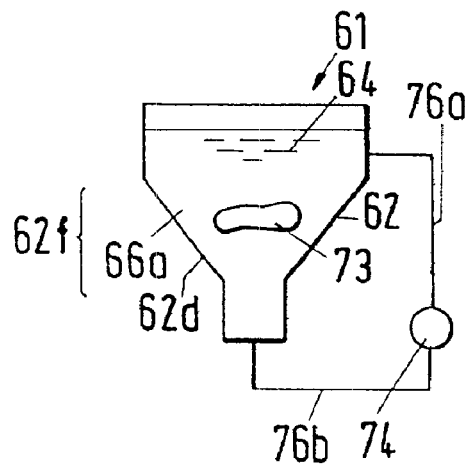

FIG. 3b shows schematically a longitudinal section through a further exemplary embodiment of a bioreactor 61, which likewise has a fluid pump 74 which is arranged outside the container 62 and which is connected to the inner space in a fluid guiding manner-via lines 76a, 76b. Along a section 62f the container 62 has an upwardly widening container wall 62d. Along this section 62f a flow develops with a flow speed which decreases upwardly, so that the inner space 66a is formed to hold the substance 73 in suspension along this section 62f.

FIG. 3c shows schematically a longitudinal section through a further exemplary embodiment of a bioreactor 61, which likewise has a fluid pump 74 which is arranged outside the container 62 and which is connected to the inner space in a fluid guiding manner via lines 76a, 76b. The line 76a opens into a section 62f in the container 62 which widens upwardly. A cylindrically designed container section 62 is arranged afterwards, within which a linear flow 64a develops and within which the substance 73 is arranged. The vertical position of the substance 73 is monitored by a sensor 85. A regulation apparatus 86 is connected in a signal conducting manner via an electrical line 85a, 86a to the sensor 85 and to the pump 74. The speed of rotation of the pump 74 is regulated in such a manner that the substance 73 remains in the region of the sensor 85.

Figure 3D:
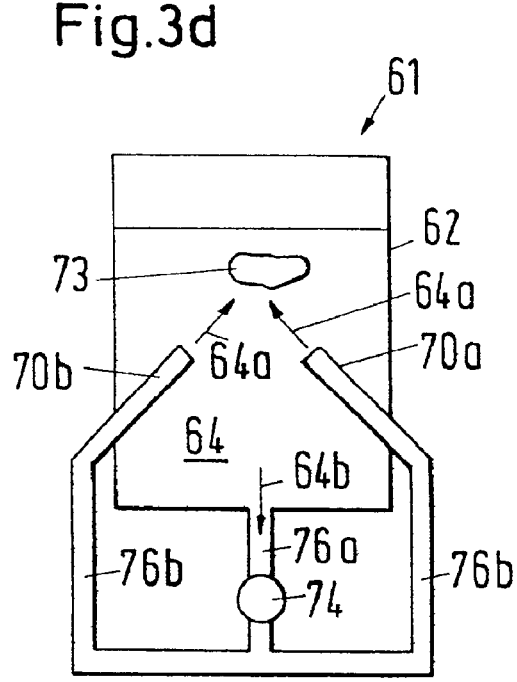

FIG. 3d shows schematically a longitudinal section through a further exemplary embodiment of a bioreactor 61, which likewise has a fluid pump 74 which is arranged outside the container 62 and which is connected in a fluid guiding manner via lines 76a, 76b to the inner space. A plurality of, for example three nozzles 70a, 70b open with orientation onto the substance 73 inside the container 62, with the flow direction which is illustrated by 64a having a flow speed which reduces in the upward direction, so that the substance 73 is supported by this flow and automatically finds an equilibrium position.

In all bioreactors 61 which are illustrated in the FIGS. 1 to 3d the substance 73 is held in a state of suspension by means of the same method, namely in that the substance 73 is acted upon with a fluid, the flow of which acts counter to the gravitational force acting on the substance 73 in such a manner that the substance 73 is held in suspension. In the exemplary embodiments in accordance with FIG. 1, 2a, 2b, 3a, 3b and 3d the fluid has a lower flow speed in the inner space 66a with increasing height. In the exemplary embodiment in accordance with FIG. 3c the speed of the fluid is regulated with a sensor 85 in dependence on the position of the substance 73.

In the exemplary embodiment in accordance with FIG. 1 a downwardly flowing flow 64c is produced within the container 62, with a gaseous fluid such as air or oxygen being led into this flow 64c. The flow speed of the flow 64c can be chosen in such a manner that the gaseous fluid which is introduced is slowed down or even no longer rises in the container 62.

Figure 4:
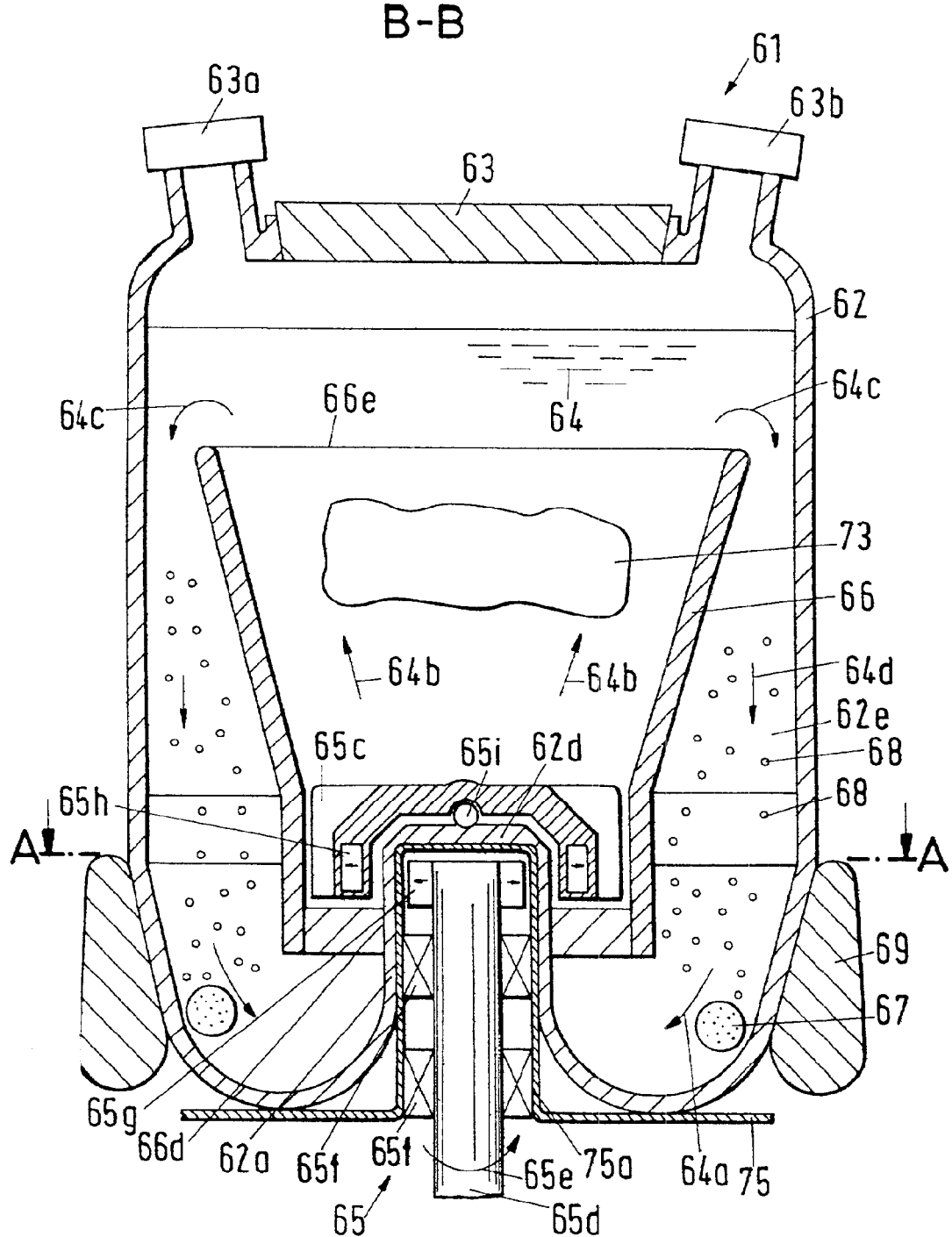
FIG. 4 is a longitudinal section along the line B—B through a further bioreactor with a magnetically coupled vaned wheel.
Figure 5:
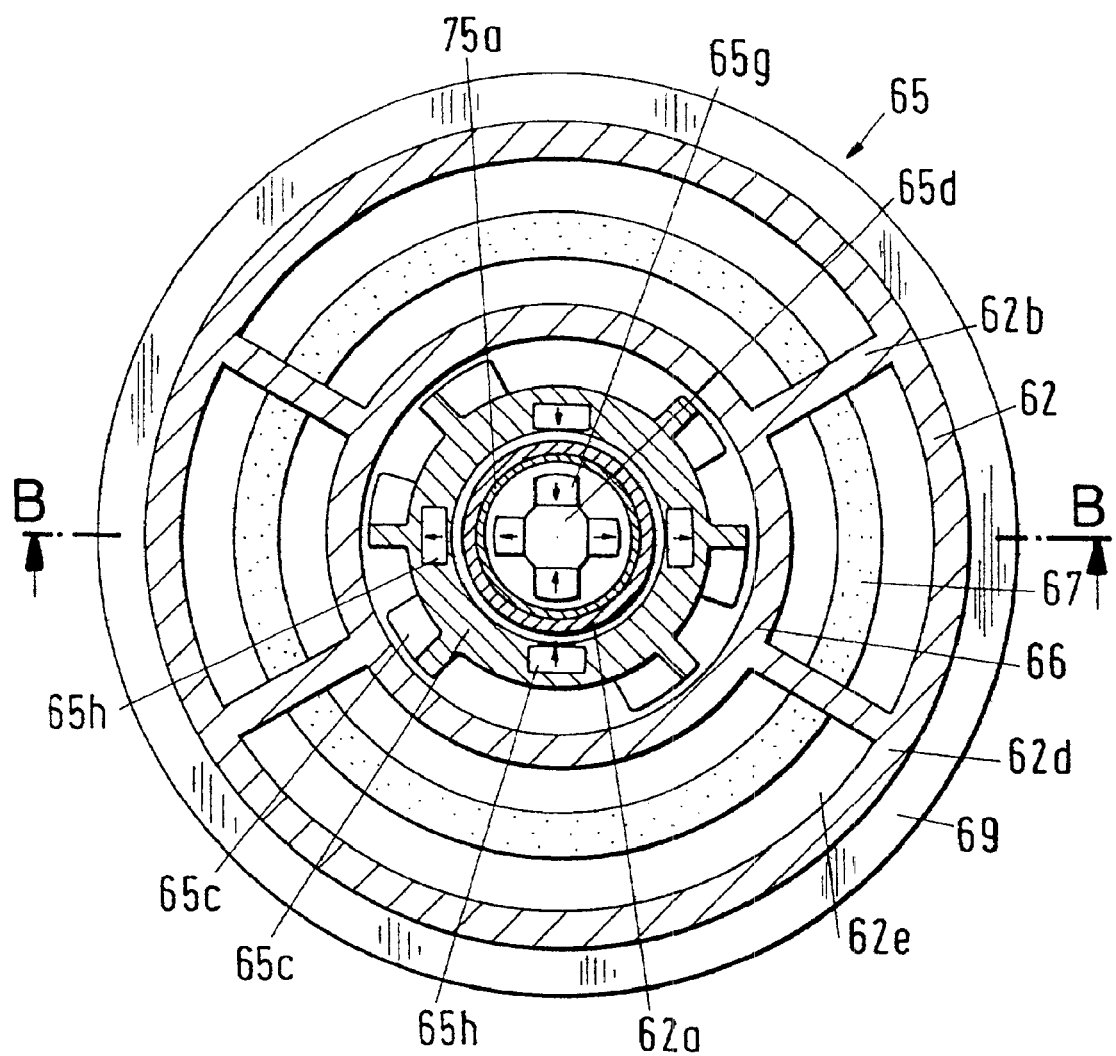
FIG. 5 is a section through FIG. 4 along the line A—A.

FIG. 4 shows a further exemplary embodiment of a bioreactor 61 in a longitudinal section along the line B—B in accordance with FIG. 5. Although otherwise designed similarly to the bioreactor 61 illustrated in FIG. 1, in the bioreactor 61 in accordance with FIG. 4, the pump 65 is arranged at the bottom in the region of the entry opening 66d of the flow guiding means 66. A vaned wheel 65c is rotatably arranged within the container 62 on a track bearing 65i, with the track bearing 65i lying on the container wall 62d. A plurality of permanent magnets 65h which are distributed around the periphery is cast into the vaned wheel 65c, which consists of a plastic. Arranged outside the container 62 is a magnetic coupling which is journalled so as to be rotatable in the direction 65e and which comprises two bearings 65f and a ring-shaped permanent magnet 65g. The rotatable shaft 65d is driven by a non-illustrated motor. A stand apparatus 75 forms a gap pot 75a which is designed to be cylindrical/and which is arranged to extend between the two permanent magnets 65g, 65h. The container wall 62d forms a gap pot section 62a at the gap pot 75a. The magnetic coupling, which comprises the permanent magnets 65h, 65i, causes the rotational motion of the rotatable shaft 65d to be transmitted to the vaned wheel 65c and the vaned wheel 65c to be held with respect to a tilting motion. The vaned wheel 65c is thus passively held magnetically.

The container 62 and the vaned wheel 65c which is rotatably journalled therein are preferably designed for a single use as an expendable product. The container 62 can be placed onto the heating apparatus 69 as well as onto the gap pot 75a, so that the container 62 is held securely and the vaned wheel 65c can be driven via the rotatably journalled magnetic coupling.

The container 62 can, as illustrated in FIG. 4, have additional openings 63a, 63b, for example for measurement probes.

FIG. 5 shows a cross-section along the line A—A in accordance with FIG. 4. Arranged in the center is the rotatable shaft 65d to which four spaced-apart permanent magnets 65g are secured. The container wall 62d of the container 62 forms a gap pot section 62a. The gap pot 75a is arranged between the gap pot section 62a and the rotatable shaft 65d with permanent magnet 65g. The gap pot section 62a is surrounded by the vaned wheel 65c, within which four permanent magnets 65h are arranged, with their polarization, illustrated by arrows, being oriented to be matched to that of the permanent magnets 65g. The flow guiding means 66 is connected via fluid guiding parts 62d to the outer wall of the container 62. The flow chamber 62e, which widens downwardly, is arranged between the flow guiding means 66 and the outer wall of the container 62. In addition the ring-shaped distributor 67 is shown.

Figure 6:
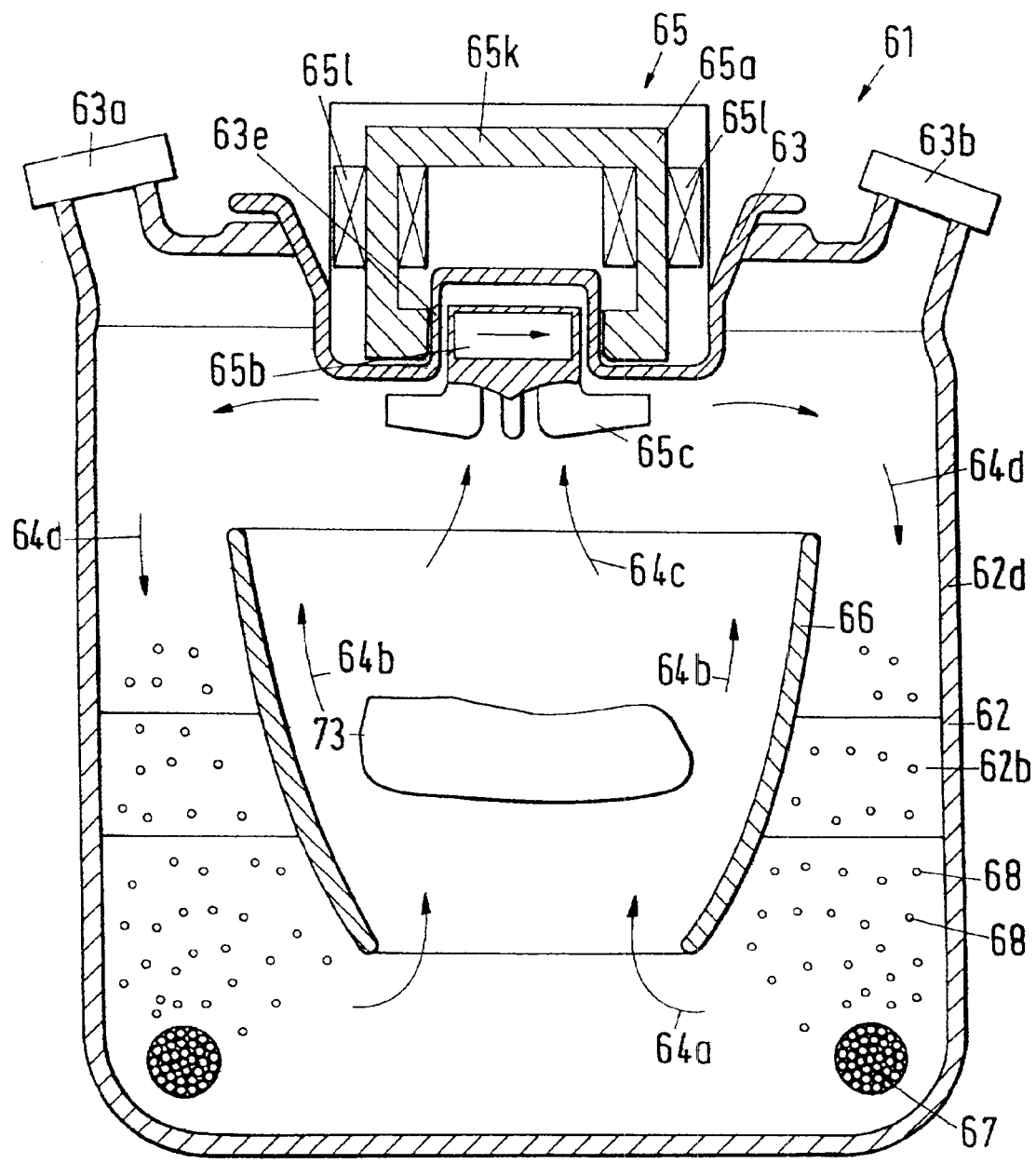
FIG. 6 is a longitudinal section through a further bioreactor with a vaned wheel which is arranged at the closeable opening.

FIG. 6 shows a longitudinal section through a further exemplary embodiment of a bioreactor 61. In contrast to the bioreactor 61 which is illustrated in FIG. 1, in the bioreactor 61 in accordance with FIG. 6 the pump 65 is arranged in the closure 63 and is designed as a centrifugal pump. The pump 65 is designed as a split tube or canned motor and comprises the firmly arranged iron stator 65a and the contact-free, rotatably journalled, rotatable part 65b, which is designed as a permanent magnet and which is firmly connected to the vaned wheel 65c. The iron stator 65a comprises a soft iron 65k which is surrounded by a plurality of coils 651. The coils 651 are arranged and can be excited in such a manner that the rotatable part 65b is driven and held without contact. The closure 63 has a gap pot section 63e, which is arranged in the gap between the iron stator 65a and the permanent magnet 65b.

An arrangement of this kind comprising a stator and a rotor which is held and driven with magnetically acting forces is also termed a temple motor and is known to the skilled person, for example from the specification WO 96/31934, in particular from its FIG. 12.

The flow guiding means 66 is firmly connected via fluid guiding parts 62b to the container wall 62d. The flow guiding means 66 has a cross-section which widens upwardly in the manner of a belly. The flow guiding means 66 can be designed in a plurality of further embodiments in such a manner that an upwardly enlarging cross-sectional area results.

Figure 7:
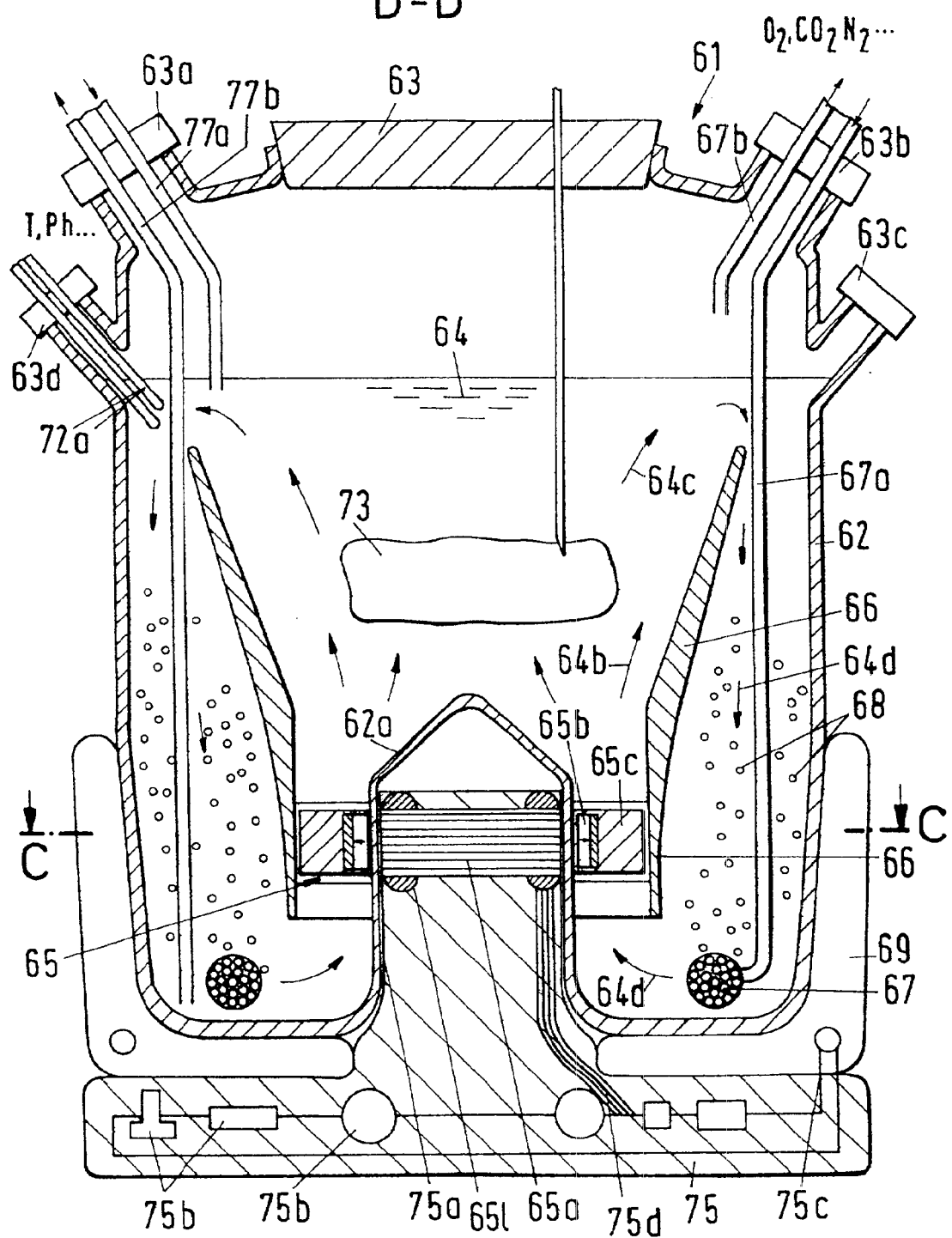
FIG. 7 is a longitudinal section along the line D—D through a further bioreactor with a magnetically coupled vaned wheel.

FIG. 7 shows a further exemplary embodiment of a bioreactor 61 in a longitudinal section along the line D—D in accordance with FIG. 8. In contrast with the bioreactor 61 which is illustrated in FIG. 4 the pump 65 has a completely magnetically journalled and driven rotatable part 65b with vaned wheel 65c. The bearingless drive of the pump 65 is illustrated in detail in cross-section along the section line C—C which is illustrated in FIG. 8. The method of functioning of a drive of this kind is for example disclosed in the specification WO 98/59406. The iron stator 65a is designed as a cross-shaped sheet metal package 65k, at the arms of which coils 651 are arranged. Through a corresponding excitation of the coils 651 a rotating magnetic field can thereby be produced. The rotatable part 65b comprises four permanent magnets 65h which are arranged in the peripheral direction, with two adjacent permanent magnets 65h in each case being polarized in opposite directions. These permanent magnets 65h are cast in or encapsulated in the vaned wheel 65c or in the pump blades 65c respectively. Sensors 65m are arranged in the stator which measure the position of the permanent magnets 65h. Electronic components 75b are arranged in the stand apparatus 75, comprising an electrical lead 75d for the coils 651 of the motor and with an electrical lead 75c for the heater 69. In addition electrical lines are arranged which connect the sensors 65m to the electronic components 75b. The coils 651 are excited in such a manner that the rotatable part 65 with pump blades 65c is held and driven without contact. The pump 65 forms an axial pump. The gap pot 75a and the gap pot section 62a of the container wall 62d are arranged between the iron stator 65a and the rotatable part 65b.

The stand apparatus 75 and the heater 69 form a firm support and holder into which the container 62 can be introduced. This arrangement has the advantage that the container 62 can be placed very simply onto the stand apparatus 75 with the heater 69, and the axial pump 65 can subsequently be operated immediately without the need for additional manipulations. The container 62 with rotatable part 65b and pump blades 65c is designed as a once-only (disposable) product, whereas the expensive components of the stand apparatus 75 and the heater 69 can be used as often as desired. In addition the stand apparatus 75 and the heater 69 need not be sterile, so that no laborious cleaning process is required. Advantages of this arrangement are the facts that the inner space of the container 62 can be kept sterile without problem and that the stand apparatus 75 can be operated without a laborious cleaning process and thus economically.

In the container 62 in accordance with FIG. 7 the inlet and outlet lines 67a, 67b for gases such as $O_2$, $CO_2$, $N_2$, pass through the closure 63b, with the inlet line 67a being connected in a fluid guiding manner to the ring-shaped distributor 67. The inlet and outlet lines 77a, 77b for the nutrient medium pass through the closure 63a. In addition, probes with probe heads 72a, for example for the measurement of temperature or pH value, pass through the closure 63d.

FIG. 9 shows schematically a longitudinal section through a further exemplary embodiment of a bioreactor 61, which likewise has a fluid pump 74 which is arranged outside the container 62 and which is connected in a fluid guiding manner to the inner space via lines 76a, 76b. The line 76b opens into the section of the flow guiding means 66 which widens upwardly. The fluid is conducted to the fluid pump 74 via the lines 76a which are arranged in the base region of the container 62, so that the fluid has the flow behavior which is indicated by the arrows 64a, 64b, 64c.

In FIG. 10 a further exemplary embodiment of the bioreactor 61 in accordance with the invention is illustrated in which cells can be cultivated. One recognizes the reaction container 62, which is surrounded here by a further vessel 84 which can, for example, contain water in order, for example, to be able to hold the reaction container 62 at a desired temperature. Arranged in the reaction container is a hollow body 66 in the shape of truncated circular cone which forms the flow guiding means 66 and which subdivides the container 62 into an upper chamber 79a and a lower chamber 79b. The jacket of the hollow body 66, in the shape of a truncated circular cone, is connected at its upper end to the wall of the reaction container 62 and tapers towards the lower end of the reaction container. The upper and lower end surfaces of the hollow body 66 are made permeable to gas and liquid, and indeed in such a manner that a membrane 80a or 80b which is designed to be permeable to gas and liquid is respectively arranged in the region of the upper and lower end surfaces. Cell carriers, for example consisting of plastic or ceramics, with cells 73, for which the membranes 80a and 80b are impermeable, can be arranged in the cavity which is enclosed between the membranes 80a and 80b. The infeed line 70 for the nutrient solution N opens in the lower chamber 79b into a ring-shaped distributor 68, which surrounds the hollow body 66. In the upper chamber 79a a suction device 81 is provided which is connected to an outlet line 71 which leads to the reservoir 82, where the nutrient solution N which is led off can be renewed or enriched with nutrients respectively. For the conveying of the nutrient solution N an expendable pump 65 or a pump with expendable parts is provided, which can for example be formed as a gear pump or as a centrifugal pump.

The nutrient solution N which is conveyed by the pump 65 out of the reservoir 82 enters into an oxygenator 83, where a gas such as for example oxygen can be admixed to the nutrient solution N or carbon dioxide removed from it. The nutrient solution N which is thus blended with oxygen or freed from carbon dioxide respectively then enters in the further course into the ring-shaped distributor 68, which is arranged in the lower chamber 79b. With the help of the expendable pump 65 and the suction device 81 a liquid flow is produced which is indicated by the arrows 64a, 64b in FIG. 5. In the region of the membrane 80b the flow speed is comparatively high; it then decreases upwardly as a result of the hollow body 66, which widens in the manner of a truncated cone. Through a suitable choice of the flow parameters or of the geometry of the hollow body 66 respectively a situation can be achieved in which the cells 73 or the substance 73 respectively are held in suspension in the region between the membranes 80b and 80a. This can favor the formation of a three-dimensional cells assembly of cells or tissue part respectively. In this exemplary embodiment the supply of nutrient solution N on the one hand and of gases such as e.g. oxygen on the other hand does not take place separately, but rather the nutrient solution N is blended with oxygen before it is introduced with the help of the infeed line 70 and the distributor 68 into the container 62.

FIG. 11 shows schematically, in a longitudinal section, a further embodiment of a bioreactor 61. This has a container 62 with a first flow chamber 66a and a second flow chamber 66f arranged above it. These two flow chambers 66a, 66f form a common inner space, which has a respective inlet opening 66d for the fluid at the top and at the bottom. A ring-like outlet opening 66e is arranged between the upper and lower inlet openings 66d by which the fluid can be supplied by means of a ring-like discharge passage 66g and the fluid line 76a to the pump 74. After the pump 74 the fluid line 76b leads through an oxygenator 83, whereupon the fluid line 76b divides into two branches which supply the fluid to the upper and/or lower inlet openings 66d. The quantity of fluid flowing in these branches can be set or controlled via the first and second clamping devices 87a, 87b. The clamping devices 87a, 87b permit the diameter of the fluid line 76b to be changed. The clamping devices 87a, 87b can for example be actuated by hand or can have electrical drive devices which are connected via non-illustrated control lines to a higher level regulating device. In an advantageous setting approximately the same quantity of fluid flows through the two branches of the fluid line 76a, so that approximately the same flow conditions arise in the first and second flow chambers 66a, 66f, but in opposite directions, so that the material or substance 63 is reliably kept in suspension within the container 62, both when buoyancy forces are acting and when gravity is acting. The substance 73 can thus be kept in suspension without an automatic regulation. The position of the material 73 can also be monitored and influenced with the aid of an automatic regulating system by detecting the position of the substance 73 with a non-illustrated sensor. Should the specific weight of the substance 73 be lighter than that of the fluid, i.e. of the nutrient solution, then the material 73 is subject to buoyancy. In this case the fluid will increasingly flow into the container 62 via the upper inlet opening 66d in order to bring about a downwardly directed fluid flow in the second flow chamber 66f, so that the substance 73 is kept in suspension by the fluid flow acting against the buoyancy. Should the specific weight of the substance 73 change in the course of time and become smaller than that of the nutrient solution, so that a downwardly acting gravitational force now acts on the substance 73, then the fluid is increasingly supplied to the lower inlet opening 66d, in order to produce an upwardly directed fluid flow in the first flow chamber 66a and thereby a buoyancy force on the substance 73. The required quantity of fluid per unit time and the division of the partial quantities to the upper and/or lower inlet openings 66d takes place manually or with a non-illustrated regulating apparatus in such a way that the substance 73 is continually kept in suspension by appropriately selected fluid flows, both with respect to a buoyancy force that is acting and also with respect to the gravitational force that is acting.

What is claimed is:

1. A method for floating at least one substance for growing a tissue part in a bioreactor, the method comprising:

providing at least one substance consisting of one of a tissue part, a scaffold having cells deposited thereon, and a scaffold including a tissue part thereon; and acting upon said substance with fluid, wherein the fluid holds the substance in free flotation;

wherein the fluid flows in a direction counter to gravity when a density of said substance is greater then a density of the fluid, and in a direction counter to buoyancy when a density of said substance is less then a density of the fluid.

2. A method in accordance with claim 1, wherein the fluid has an increasingly lower flow speed in the direction counter to gravitation.

3. A method in accordance with claim 1, wherein the substance is acted upon with at least one fluid jet.

4. A method in accordance with claim 1, wherein a position of the substance in the bioreactor is measured by a sensor, and wherein a speed of the fluid in the bioreactor is regulated to hold the substance in flotation.

5. A method in accordance with claim 1, wherein the fluid flows downward in the direction of gravitation, and wherein a gaseous fluid is led into the downward flowing fluid.

6. A method in accordance with claim 5, wherein a flow of the gaseous fluid is slowed down by a flow of the downward flowing fluid.

7. A method in accordance with claim 5, wherein the gaseous fluid is oxygen.

8. A method in accordance with claim 5, wherein the gaseous fluid is air.

9. A bioreactor for growing a tissue part comprising:

a container comprising a first flow chamber;

at least one substance consisting of one of a tissue part, a scaffold having cells deposited thereon, and a scaffold including a tissue part thereon, wherein the substance is acted upon with fluid; and an apparatus for conveying the fluid, wherein the substance is arranged in the first flow chamber in such a manner that the fluid holds the substance in free flotation.

10. A bioreactor in accordance with claim 9 further comprising:

a sensor; and a regulation apparatus, wherein the fluid conveying apparatus is connected to the first flow chamber, and wherein the regulation apparatus is connected to the fluid conveying apparatus and to the sensor in such a manner that the position of the substance may be measured and regulated.

11. A bioreactor in accordance with claim 9, wherein the first flow chamber widens upwardly.

12. A bioreactor in accordance with claim 11, wherein the container has a section of the wall, wherein said section widens upwardly and forms the first flow chamber.

13. A bioreactor in accordance with claim 9, wherein at least one fluid line opens into the first flow chamber.

14. A bioreactor in accordance with claim 13 wherein the at least one fluid line is arranged such that it opens into the first flow chamber from below with respect to the first flow chamber.

15. A bioreactor in accordance with claim 13 wherein the at least one fluid line is arranged such that it opens into the first flow chamber laterally with respect to the first flow chamber.

16. A bioreactor in accordance with claim 9 further comprising at least one fluid guiding means arranged in the container, wherein the fluid guiding means forms the first flow chamber, and wherein the first flow chamber widens upwardly.

17. A bioreactor in accordance with claim 16, wherein the fluid guiding means is a hollow body.

18. A bioreactor in accordance with claim 17, wherein the hollow body has an inner space, and wherein said inner space widens upwardly and forms the first flow chamber.

19. A bioreactor in accordance with claim 17, wherein the container comprises a wall, wherein the hollow body has an upwardly reducing outer contour, and wherein the hollow body is arranged in the container in such a manner that the first flow chamber is formed between said outer contour and the container wall.

20. A bioreactor in accordance with claim 17, wherein the hollow body is formed in the shape of a truncated circular cone.

21. A bioreactor in accordance with claim 9, wherein the container has at least one closeable opening.

22. A bioreactor in accordance with claim 21, wherein the closeable opening has a surface of at least one fourth of a cross-sectional area of the container.

23. A bioreactor in accordance with claim 21, wherein the closeable opening is arranged above the first flow chamber.

24. A bioreactor in accordance with claim 9, wherein the fluid conveying apparatus is outside the container, and wherein the fluid conveying apparatus is connected to the container.

25. A bioreactor in accordance with claim 9, wherein the fluid conveying apparatus comprises a fluid conveying means arranged inside the container.

26. A bioreactor in accordance with claim 25, wherein the fluid conveying apparatus comprises an electric motor having a static motor part arranged outside the container and a rotatable motor part arranged inside the container, and wherein the fluid conveying means is connected to the rotatable motor part.

27. A bioreactor in accordance with claim 26, wherein the electric motor is a canned motor, and wherein the rotatable motor part is rotated without a through-going shaft.

28. A bioreactor in accordance with claim 26, wherein the fluid conveying apparatus comprises a magnetic coupling drive adapted for coupling to the rotatable motor part.

29. A bioreactor in accordance with claim 26, wherein the rotatable motor part is journalled at least with respect to one degree of freedom with magnetically acting means.

30. A bioreactor in accordance with claim 29, wherein the rotatable motor part is completely magnetically journalled.

31. A bioreactor in accordance with claim 25, wherein the fluid conveying means is a vaned wheel.

32. A bioreactor in accordance with claim 9 further comprising a second flow chamber arranged above the first flow chamber, wherein the second flow chamber is formed in such a manner that fluid flowing from top to bottom therein has a lower speed with decreasing height.

33. A bioreactor in accordance with claim 32, wherein the first and the second flow chambers form a common inner space which has an inlet opening for the fluid at the top and at the bottom and which has an outlet opening between the top and bottom inlet opening.

34. A bioreactor in accordance with claim 32, wherein the fluid conveying means is a pump that is connected to the top and bottom inlet opening and to the outlet opening in such a manner that the quantity of fluid flowing into the top and bottom inlet opening may be controlled.

35. A method for floating a substance for growing a tissue part in a bioreactor, the method comprising:

providing at least one substance consisting of at least one of a tissue part, a scaffold having cells deposited thereon, and a scaffold including one or more tissue parts thereon; and acting upon said substance with fluid, wherein the fluid holds the substance in free flotation;

wherein the fluid flows in a direction counter to gravity when a density of said substance is greater then a density of the fluid, and in a direction counter to buoyancy when a density of said substance is less then a density of the fluid.

36. A method in accordance with claim 35, wherein the substance is acted upon with at least one fluid jet.

37. A method in accordance with claim 35, wherein a position of the substance in the bioreactor are measured by a sensor, and wherein a speed of the fluid in the bioreactor is regulated to hold the substance in floatation.

38. A method in accordance with claim 35, wherein the fluid flows downward in the direction of gravity, and wherein a gaseous fluid is led into the downward flowing fluid.

39. A method in accordance with claim 38, wherein a flow of gaseous fluid is slowed down by a flow of the downward flowing fluid.

40. A method in accordance with claim 35, wherein the fluid has an increasingly lower speed in the direction counter to gravity.

41. A bioreactor comprising a container for a substance, the bioreactor comprising:

a first flow chamber to which a flowing fluid may be supplied, with the first flow chamber being designed such that the fluid flowing upwardly therein has a lower speed with increasing height; and a second flow chamber arranged above the first flow chamber, the second flow chamber being designed such that fluid flowing from top to bottom within the second flow chamber has a smaller speed with decreasing height;

wherein the first flow chamber and the second flow chamber form a common inner space that has a first inlet opening for the fluid at a top of the common inner space and a second inlet opening for the fluid at a bottom of the common space; and wherein the common inner space has an outlet opening between the first and second inlet openings.

* * * * *